(12) United States Patent
Coute et al.

(10) Patent No.: US 7,253,005 B2
(45) Date of Patent: Aug. 7, 2007

(54) CATALYST SAMPLING SYSTEM

(75) Inventors: Nicolas P. Coute, Houston, TX (US);
James R. Lattner, Seabrook, TX (US);
Jeffrey Scott Smith, Seabrook, TX (US);
Carl Edward Manning, Missouri City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 594 days.

(21) Appl. No.: 10/652,476

(22) Filed: Aug. 29, 2003

(65) Prior Publication Data
US 2005/0047965 A1 Mar. 3, 2005

(51) Int. Cl.
G01N 1/00 (2006.01)
G01N 25/26 (2006.01)
G01N 33/24 (2006.01)
G01N 1/20 (2006.01)

(52) U.S. Cl. .................. 436/174; 436/31; 436/158; 73/863.71; 73/863.81; 73/864.81; 73/864.85; 73/64.56

(58) Field of Classification Search .............. 436/31
See application file for complete search history.

(56) References Cited

U.S. PATENT DOCUMENTS

| | | | | |
|---|---|---|---|---|
| 3,575,055 A | * | 4/1971 | Thornton, Jr. | ............ 73/863.43 |
| 3,614,230 A | * | 10/1971 | Crawford | ...................... 356/36 |
| 3,653,265 A | * | 4/1972 | Vallino et al. | ............ 73/863.83 |
| 3,786,682 A | | 1/1974 | Winter et al. | ............. 73/421 B |
| 4,594,270 A | | 6/1986 | Brooks | ........................ 427/213 |
| 4,854,180 A | | 8/1989 | Mauleon et al. | .......... 73/863.86 |
| 5,430,301 A | * | 7/1995 | Shofner et al. | ........... 250/461.1 |
| 6,592,827 B1 | * | 7/2003 | Zilker et al. | ................. 422/119 |

OTHER PUBLICATIONS

Anonymous: "Automatic Extraction and Conditioning Method for Solid Polymer Sample", Research Disclosure, Kenneth Mason Publications, Hampshire, GB, vol. 352, No. 5, Aug. 1993.
Brun-Tsekhovoi et al., "Equipment Suited for taking Samples of a Granular Solid Material From Apparatus Operated at High Pressure," *Institute of Petrochemical Synthesis, Academy of Sciences of USSR*. Translated from Khimiya I Teckhnoiogiya Topliv I Masel, No. 9, pp. 44, Sep. 1972.

* cited by examiner

Primary Examiner—Jill Warden
Assistant Examiner—Keri A Moss

(57) ABSTRACT

A method and apparatus are provided for obtaining a reproducible sample of solid particles. The reproducible sample is obtained by receiving solid particles into a collection system that includes a sheltered volume. Solid particles that settle outside of the sheltered volume are purged from the collection system. The remaining solid particles inside the sheltered volume correspond to the reproducible sample.

33 Claims, 3 Drawing Sheets

CATALYST SAMPLING SYSTEM

FIELD OF THE INVENTION

This invention relates to methods and structures for obtaining samples of solid particles. In particular, this invention relates to methods and structures for extracting samples of solid particles from reactors containing fixed or fluidized beds of solid particles.

BACKGROUND OF THE INVENTION

Fluidized beds of solid particles are employed in a variety of reactors, such as methanol to olefin (MTO) reactors, gas-phase polymerization reactors, and catalytic cracking reactors. Fluidized beds can also be found in reactors for treatment of pollutants via advanced oxidation processes. In reactors using a fluidized bed of solid particles, the solid particles typically serve as catalysts for the desired chemical reaction. For example, in MTO reactors the desired reaction is the conversion of methanol to an olefin such as ethylene or propylene. Methanol feedstock is passed through a fluidized bed of solid particles that catalyze this conversion.

One way to achieve greater control over the reaction in a reactor with a fluidized bed of solid particles is to monitor the state of the particles. Monitoring the condition of the solid particles within the reactor provides information for process adjustments to increase efficiency. For example, during operation of an MTO reactor, the solid catalyst particles in the fluidized bed will typically acquire some amount of amorphous carbon coating. This is sometimes referred to as 'coking' of the catalyst particles. Because the level of coking on the catalyst particles directly impacts the efficiency of the conversion reaction, MTO reactors typically include a regeneration system for reducing the level of coking on the catalyst particles. Monitoring the level of coking on the particles provides feedback for controlling this regeneration process.

Monitoring the state of the catalyst particles requires removal of a sample of the solid particles from the fluidized bed. Some current solid sampling methods for fluidized beds make use of lock hoppers with interlocked valves. A lock hopper refers to a volume within in an apparatus that can be isolated from the rest of the apparatus. Lock hopper designs are often employed to allow transfer of material between sections of an apparatus that operate at different pressures. In a system for collecting a sample of solid particles from a fluidized bed, the lock hopper is used to reduce the pressure of a sample from the higher pressure of the fluidized bed to a lower pressure (such as ambient) for testing of the sample. The interlocked valves prevent opening of a continuous path of valves that would allow escape of the pressurized particles from the fluidized bed.

An example of the lock hopper concept for sampling fluidized solids is shown in U.S. Pat. No. 3,614,230. According to the patent, a sample is drawn through a series of valves into a "deflaidization zone," where the sample is isolated from the fluidized bed. This allows any fluidization gas (and excess pressure) to be removed from the sample by use of a filter. The amount of sample collected is determined by the amount of time the valves are left open After defluidization, the sample is transferred to another chamber for further processing.

One of the shortcomings of the aforementioned systems for sampling solid particles is that it is difficult to reproducibly collect a sample of a particular size. For example, in the apparatus used in U.S. Pat. No. 3,614,230, the size of the solid particle sample depends on the length of time the appropriate valves remain open as well as the flow rate of solid particles into the sampling system. As a result, the size of a solid particle sample collected in these conventional systems will be sensitive to small changes in process conditions.

What is needed is an effective method for collecting a small, reproducible sample of solid particles from a fluidized bed. The method should be self-limiting, so that precise timing is not needed to maintain a consistent size between successive solid particle samples. The method should also be easy to use, to allow for repeated sampling of a process if desired.

SUMMARY OF THE INVENTION

In one embodiment, the present invention provides a method for obtaining a predetermined volume of solid material from a reactor system. In this embodiment, the method begins by receiving solid material from the reactor system and collecting the solid material in a sample collection system. A portion of the solid material is then removed from the sample collection system by passing a gas through the sample collection system. This leaves behind a predetermined volume of solid material in the sample collection system. The predetermined volume of solid material is then extracted from the sample collection system.

In another embodiment, the sample collection system can comprise an unsheltered volume connected to a sheltered volume. In such an embodiment, the portion of the solid material removed from the sample collection system by passing a gas through the collection system corresponds to solid material in the unsheltered volume. The predetermined volume of material left behind is material in the sheltered volume. In an embodiment, the collection system can be purged prior to receiving the solid material from the reactor system.

In an embodiment, the solid material is received from a fluidized bed reaction system, a fast fluidized bed reaction system, a circulating fluidized bed reaction system, or a riser reactor system. In another embodiment, the solid material is received from a catalytic cracking reactor. In still another embodiment, the solid material is received from a reaction system selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates to olefins, systems for converting oxygenates to aromatics, systems for oligomerizing olefins, and systems for converting unsaturated hydrocarbons to aldehydes.

In an embodiment, the received solid material is composed of solid particles containing a catalytically active component and a matrix material. In another embodiment, the catalytically active component is selected from the group consisting of metal, metal oxides, zeolites, silicaaluminophosphates, and molecular sieves.

In another embodiment, the present invention provides a method for obtaining a sample of solid particles. In this embodiment, the method begins by receiving a sample of solid particles that comprises a first portion and a second portion. The second portion of the sample is then separated from the first portion of the sample. Finally, the first portion of the sample is extracted for further use.

In an embodiment, the first portion of the sample is collected in a sheltered volume prior to separating the second portion of the sample from the first portion of the sample. In another embodiment, the sheltered volume corresponds to a predetermined sample volume. In an embodiment, receiving the sample of solid particles comprises entraining the sample of solid particles in a gas flow and then drawing the entrained solid particles into a collection system.

In an embodiment, the sample of solid particles is received from a fluidized bed reaction system, a fast fluidized bed reaction system, a circulating fluidized bed reaction system, or a riser reactor system. In another embodiment, the sample of solid particles is received from a catalytic cracking reactor. In still another embodiment, the solid material is received from a reaction system selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates to olefins, systems for converting oxygenates to aromatics, systems for oligomerizing olefins, and systems for converting unsaturated hydrocarbons to aldehydes.

In an embodiment, the sample of solid particles is composed of solid particles containing a catalytically active component and a matrix material. In another embodiment, the catalytically active component is selected from the group consisting of metal, metal oxides, zeolites, silicaaluminophosphates, and molecular sieves.

In another embodiment, the present invention provides an apparatus for obtaining a sample of solid particles. In this embodiment, the apparatus comprises a particle intake conduit connected to a solid particle source. A sheltered volume is connected to the particle intake conduit, wherein the connection between the sheltered volume and the particle intake conduit defines a first flow path. A purge source is connected to the first flow path between the particle intake conduit and the sheltered volume. An exhaust is also connected to the first flow path with the connection between the exhaust and the first flow path defining a second flow path. The exhaust is connected so that at least a portion of the first flow path and second flow path are in common, and the second flow path does not pass through the sheltered volume.

In an embodiment, the sheltered volume can further comprise a filter having a smaller mesh size than the average particle size of the solid particles. In another embodiment, the particle intake conduit can be connected to the solid particle source via a particle intake valve. Similarly, the sheltered volume can be connected to the particle intake conduit via a sampling valve. In still another embodiment, the first flow path, sheltered volume, and exhaust can come together in the form of a "T" intersection. In yet another embodiment, the common portion of the flow paths is immediately adjacent to the sheltered volume.

In an embodiment, the solid particle source is a fluidized bed reaction system, a fast fluidized bed reaction system, a circulating fluidized bed reaction system, or a riser reactor system. In another embodiment, the solid particle source is a catalytic cracking reactor. In still another embodiment, the solid material is received from a reaction system selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates to olefins, systems for converting oxygenates to aromatics, systems for oligomerizing olefins, and systems for converting unsaturated hydrocarbons to aldehydes.

In an embodiment, the solid particle source is composed of solid particles containing a catalytically active component and a matrix material. In another embodiment, the catalytically active component is selected from the group consisting of metal, metal oxides, zeolites, silicaaluminophosphates, and molecular sieves.

In still another embodiment, the present invention provides a method for obtaining a sample of solid particles. In this embodiment, a collection system is provided that comprises a particle intake conduit connected to a source of solid particles, a source of purge gas, an exhaust, a sheltered volume, a first flow path connecting the particle intake conduit to the sheltered volume, and a second flow path connecting the source of the purge gas and the exhaust. In this embodiment, at least a portion of the first flow path and at least a portion of the second flow path are in common. Also, the second flow path does not pass through the sheltered volume. In this embodiment, a sample of solid particles is received into the sheltered volume via the first flow path. Purge gas is then flowed through the common portions of the flow paths. The sample of solid particles is then extracted from the sheltered volume.

In an embodiment, the collection system can be purged prior to receiving the sample of solid particles. In another embodiment, solid particles are received into the collection system by opening a particle intake valve for a period of one second, wherein the particle intake valve connects the particle intake conduit to the source of solid particles. Additionally, the solid particles can be extracted from the sheltered volume by disconnecting the sheltered volume from the collection system.

In an embodiment, the sample of solid particles is received from a fluidized bed reaction system, a fast fluidized bed reaction system, a circulating fluidized bed reaction system, or a riser reactor system. In another embodiment, the sample of solid particles is received from a catalytic cracking reactor. In still another embodiment, the solid material is received from a reaction system selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates to olefins, systems for converting oxygenates to aromatics, systems for oligomerizing olefins, and systems for converting unsaturated hydrocarbons to aldehydes.

In an embodiment, the sample of solid particles is composed of solid particles containing a catalytically active component and a matrix material. In another embodiment, the catalytically active component is selected from the group consisting of metal, metal oxides, zeolites, silicaaluminophosphates, and molecular sieves.

BRIEF DESCRIPTION OF THE DRAWINGS

Examples of various embodiments of this invention are shown in the attached Figures, wherein.

DETAILED DESCRIPTION OF THE INVENTION

I. Overview of Sample Collection

Figure 1:
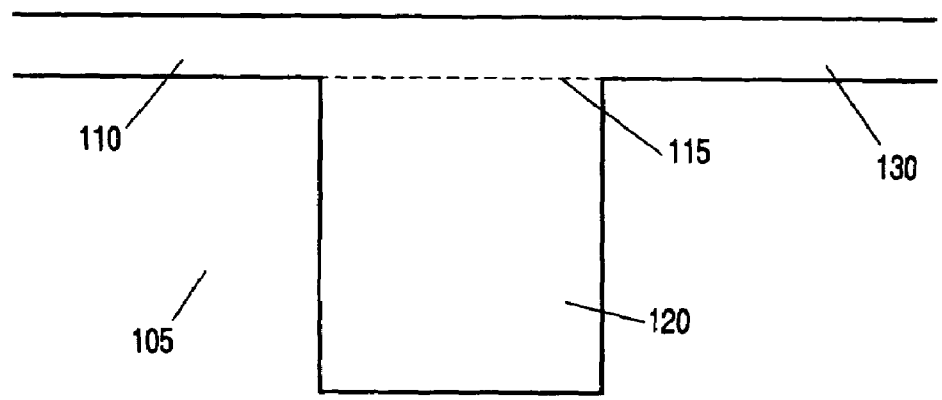
FIG. 1 schematically shows an example of a sheltered volume within a sampling system.

This invention is directed to methods for collecting a solid particle sample from a reactor system containing a bed of solid particles. In particular, the present invention allows for collection of a sample of a reproducible size based on mechanical and structural constraints. Precisely timed opening and closing of valves is not required. Due to the self-limiting nature of the collection method, the size of the collected sample will be insensitive to variations in the collection process.

During sample collection, solid particles are drawn into a collection system. Typically the solid particles will be entrained in a gas flow. Particles are allowed to enter the collection system until an amount greater than the desired sample size has been drawn in. The collection system is then purged. During the purge operation, purge gas flows from the purge gas source to the exit or exhaust for the sample collection apparatus. Any particles in the flow path of the purge gas will be swept along to the exhaust. However, particles not in the flow path of the purge gas remain in the collection system. These particles remaining in the collection system after the purge constitute the desired sample, which is extracted from the collection system for further use.

A variety of structures can be used to collect particles so that at least a portion of the collected particles lie outside of the flow path of the purge gas in the collection system. For example, the particles outside of the purge gas flow path can be collected in a pipe that branches off from the main pipe or conduit. During particle collection, the exhaust is closed off, such as by closing an exhaust valve. This prevents the flow of solid particles from exiting the collection system. Instead, the flow of solid particles will be distributed throughout the collection system, including structures such as the branched pipe.

In this embodiment, the branched pipe contains a valve or a filter with a mesh size smaller than the average particle size of the solid particles. As solid particles enter the branched pipe, the solid particles cannot travel past the valve or filter. The distance from the valve or filter to the branching point from the main pipe or conduit defines the volume where particles are collected in the branched pipe. Particle collection continues until the volume from the branching point to the valve or filter is filled with solid particles. After particle collection, the exhaust valve is opened and the system is purged. This provides a continuous flow path from the source of the purge gas to the exhaust. This allows the purge gas to flow directly from the purge source to the exhaust without passing through the branched pipe. As a result, particles that settle within the branched pipe remain outside of the flow path of the purge gas during the purge step.

In another embodiment, the particles can be collected in a compartment that is openly connected to a conduit that is part of the flow path for the purge gas. In this embodiment, the compartment is openly connected to the bottom of the conduit. When particles are drawn into the system, the particles collect in the bottom of the compartment. During a purge step, the purge gas will pass over the top of the particles within the compartment, leaving the particles in the compartment outside of the purge gas flow path.

The solid particles entering the collection system are typically drawn in from a fluidized bed or similar solid particle source. In preferred embodiments, solid particles are drawn into the collection system due to the pressure differential between the fluidized bed and the collection system. At the beginning of sample collection, the pressure within the collection system will typically be ambient, although the collection system may be at any pressure so long as it is well below the pressure of the fluidized bed. By contrast, the necessary conditions for creating a fluidized bed require elevated pressures within the fluidized bed. When a connection is opened between the fluidized bed and the collection system, the pressure differential induces a flow of gas from the fluidized bed into the collection system. This causes solid particles entrained in this gas flow to be carried into the collection system as well.

After removing any solid particles residing in the flow path of the purge gas, the remaining solid particles are extracted. In some embodiments, this can involve opening a valve to allow the release of the particles. In other embodiments, the sample of solid particles is extracted for further use by disconnecting the volume containing the solid particles from the rest of the collection apparatus. In these embodiments, the volume containing the solid particles is isolated from the rest of the collection system, such as by closing off valves. The volume containing the solid particles is then removed to allow extraction of the sample of solid particles.

II. Examples of Structure for Collecting Solid Particles

An embodiment of the invention is represented in FIG. 1. Specifically, FIG. 1 depicts a schematic example of a structure 105 within a collection system where particles can reside during a purge operation without being affected by the purge gas. Particles entering the collection system pass through pipe or conduit 110 and travel toward volume or compartment 120. The dotted line defines the boundary between pipe 110 and compartment 120 in FIG. 1. As particles reach compartment 120, the particles begin to fill the volume. Particles will continue to fill compartment 120 until it fills, causing any additional particles to flow into exhaust 130.

After collecting particles, the collection system is purged. Pipe or conduit 110 is also part of the flow path for purge gas during a purge operation for the collection system. When the system is purged, purge gas passes through pipe 110 and toward exhaust 130. Particles collected in compartment 120, however, are not purged from the system. In FIG. 1, particles residing below the dotted line are not in the flow path of the purge gas. As a result, the particles below the dotted line will remain in compartment 120 during a purge operation. Only the particles above the dotted line will be removed from the system as the purge gas travels from pipe 110 to exhaust 130. This facilitates collection of a sample of a predetermined size that corresponds to the size of compartment 120. As long as the particle collection step lasts long enough to fill compartment 120, a volume of solid particles corresponding to the size of the compartment should be collected each time under this method. The size of compartment 120 can be any size that corresponds to a desired or convenient volume for a sample.

After the particle collection step, solid particles not in compartment 120 are removed from the collection system by purging the particles toward exhaust 130. The particles purged from the system will preferably be trapped in a filter at the end of the exhaust. In some embodiments, solid particles purged into the exhaust are eventually recycled back into the particle bed.

Figure 2:
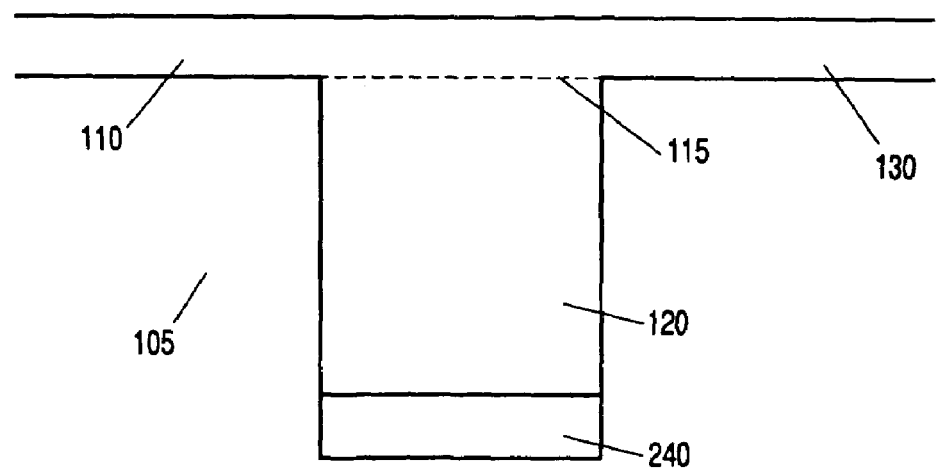
FIG. 2 schematically depicts another sheltered volume configuration.

FIG. 2 schematically depicts another structure according to the present invention that can be employed within a collection system. In FIG. 2, the bottom boundary of compartment 120 is a filter 240 with a mesh size smaller than the size of the solid particles. Filter 240 permits gases traveling with the solid particles, such as an entrainment gas, to escape while still retaining the solid particles. During particle collection, gases passing through filter 240 are preferably captured in a closed volume, such as a sample bomb. Allowing gases to flow out of compartment 120 during particle collection reduces the likelihood of incomplete filling of the compartment.

Structures such as compartment 120 or the previously described branched pipe serve as "sheltered volumes" within a collection apparatus. The sheltered volume is a portion of a collection system where solid particles can be retained during a typical purge operation. In a collection system that uses a purge gas to remove solid particles from the system, the sheltered volume is a volume within the system that resides outside of the flow path of the purge gas. Other structures which can serve as a sheltered volume will be apparent to those of skill in the art.

III. Types of Solid Particle Sources

The sampling method and apparatus of the present invention can be used to obtain a solid particle sample from any type of reaction system containing a suitable source of solid particles. A reaction system will typically comprise at least one reactor unit. Optionally, a reaction system can contain two or more reactor units. The reactor units can be in series or parallel. Non-limiting examples of reaction systems that can be sampled using the methods and apparatus of this invention include fluidized bed reaction systems, fast fluidized bed reaction systems, circulating fluidized bed reaction systems, riser reactor systems, and the like. Suitable conventional reaction systems and reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference. Other examples of reaction systems include riser reactors, such as those generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which references are all herein fully incorporated by reference.

The present invention can be used with any type of reaction system involving the aforementioned types of solid particle sources. Non-limiting examples of such reaction systems include reaction systems selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates (e.g., alcohols) to olefins, systems for converting oxygenates (e.g., alcohols) to aromatics, systems for oligomerizing olefins, and systems for converting unsaturated hydrocarbons to aldehydes. More specifically, such examples include:

A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (time of contact of feed and/or product with catalyst) from about 10 milliseconds to about 10 seconds;

B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 $hr^{-1}$ to about 100 $hr^{-1}$;

C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 $hr^{-1}$ to about 100 $hr^{-1}$, and an aromatic hydrocarbon/polyalkylaromatic hydrocarbon mole ratio of from about 1/1 to about 16/1;

D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 $hr^{-1}$ to about 200 $hr^{-1}$, and a hydrogen/hydrocarbon mole ratio of from about 0 to about 100/1;

E) The catalytic dewaxing of hydrocarbons by selectively removing straight chain paraffins. The reaction conditions are dependent in, large measure on the feed used and upon the desired pour point. Typical reaction conditions include a temperature between about 200° C. and 450° C., a pressure of up to 3,000 psig and a liquid hourly space velocity from 0.1 $hr^{-1}$ to 20 $hr^{-1}$.

F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 hr$^{-1}$ to about 100 hr$^{-1}$, and an aromatic hydrocarbon/alkylating agent mole ratio of from about 1/1 to about 20/1;

G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 hr$^{-1}$ to about 2000 hr$^{-1}$, and an aromatic hydrocarbon/olefin mole ratio of from about 1/1 to about 20/1. The resulting products from the reaction are long chain alkyl aromatics, which when subsequently sulfonated have particular application as synthetic detergents;

H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 hr$^{-1}$ to about 50 hr$^{-1}$;

I) The hydrocracking of heavy petroleum feedstocks, cyclic stocks, and other hydrocrack charge stocks. The catalyst will contain an effective amount of at least one hydrogenation component;

J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 psig to about 800 psig, a WHSV-olefin from about 0.4 hr$^{-1}$ to about 0.8 hr$^{-1}$, a WHSV-reformate of from about 1 hr$^{-1}$ to about 2 hr$^{-1}$ and, optionally, a gas recycle from about 1.5 to about 2.5 vol/vol fuel gas feed;

K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 100° C. to about 400° C. and pressures from about 50 psig to 450 psig;

L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 hr$^{-1}$ to about 10 hr$^{-1}$;

M) The conversion of light paraffins to olefins and/or aromatics. Typical reaction conditions include temperatures from about 425° C. to about 760° C. and pressures from about 10 psig to about 2000 psig;

N) The conversion of light olefins to gasoline, distillate and lube range hydrocarbons. Typical reaction conditions include temperatures of from about 175° C. to about 375° C., and a pressure of from about 100 psig to about 2000 psig;

O) Two-stage hydrocracking for upgrading hydrocarbon streams having initial boiling points above about 200° C. to premium distillate and gasoline boiling range products or as feed to further fuels or chemicals processing steps. Either stage of the two-stage system can contain catalyst, which contains molecular sieve that is susceptible to loss of catalytic activity due to contact with water molecules. Typical reaction conditions include temperatures of from about 315° C. to about 455° C., pressures of from about 400 to about 2500 psig, hydrogen circulation of from about 1000 SCF/bbl to about 10,000 SCF/bbl and a liquid hourly space velocity (LHSV) of from about 0.1 hr$^{-1}$ to 10 hr$^{-1}$;

P) A combination hydrocracking/dewaxing process in the presence of a catalyst that contains molecular sieve that is susceptible to loss of catalytic activity due to contact with water molecules. The catalyst generally further comprises a hydrogenation component. Optionally included in the catalyst is zeolite molecular sieve such as zeolite Beta. Typical reaction conditions include temperatures from about 350° C. to about 400° C., pressures from about 1400 psig to about 1500 psig, LHSVs from about 0.4 hr$^{-1}$ to about 0.6 hr$^{-1}$ and a hydrogen circulation from about 3000 to about 5000 SCF/bbl;

Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-zeolite) from about 0.1 hr$^{-1}$ to about 200 hr$^{-1}$ and an alcohol to olefin molar feed ratio from about 0.1/1 to about 5/1;

R) The disproportionation of aromatics, e.g., the disproportionation toluene to make benzene and paraxylene. Typical reaction conditions include a temperature of from about 200° C. to about 760° C., a pressure of from about atmospheric to about 60 atmosphere (bar), and a WHSV of from about 0.1 hr$^{-1}$ to about 30 hr$^{-1}$;

S) The conversion of naphtha (e.g., $C_6$-$C_{10}$) and similar mixtures to highly aromatic mixtures. Thus, normal and slightly branched chained hydrocarbons, preferably having a boiling range above about 40° C., and less than about 200° C., can be converted to products having a substantially higher octane aromatics content by contacting the hydrocarbon feed with a molecular sieve catalyst at a temperature of from about 400° C. to 600° C., preferably from about 480° C. to about 550° C., at pressures of from atmospheric to 40 bar, and liquid hourly space velocities (LHSV) of from 0.1 hr$^{-1}$ to 15 hr$^{-1}$;

T) The adsorption of alkyl aromatic compounds for the purpose of separating various isomers of the compounds;

U) The conversion of oxygenates, e.g., alcohols, such as methanol, or ethers, such as dimethylether, or mixtures thereof to hydrocarbons including olefins and aromatics with reaction conditions including temperatures of from about 275° C. to about 600° C., pressures of from about 0.5 atmosphere to about 50 atmospheres, and a liquid hourly space velocity of from about 0.1 hr$^{-1}$ to about 100 hr$^{-1}$;

V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a molecular sieve catalyst at a temperature in the range of from about 250° C. to about 800° C., a LHSV of from about 0.2 hr$^{-1}$ to about 50 hr$^{-1}$, and a hydrocarbon partial pressure of from about 0.1 to about 50 atmospheres. Temperatures below about 250° C. may be used to oligomerize the feedstock when the feedstock is in the liquid phase when contacting the coated zeolite catalyst. Thus, when the olefin feedstock contacts the catalyst in the liquid phase, temperatures of from about 10° C. to about 250° C. may be used;

W) The conversion of $C_2$ unsaturated hydrocarbons (ethylene and/or acetylene) to aliphatic $C_{6-12}$ aldehydes and converting the aldehydes to the corresponding $C_{6-12}$ alcohols, acids, or esters.

X) The reaction of silicon with methyl chloride to ultimately form silicones via the "Direct Process." The reaction of silicon with methyl chlorides produces methylchlorosilanes, which are then hydrolyzed to produce silicones.

Y) The reaction of $C_4$ hydrocarbons with oxygen to form maleic anhydride.

While the particle collection apparatus and method of this invention can be used with a reaction system of any size, the present invention is particularly suited to sampling in large, commercial scale reaction systems. For example, the particle collection apparatus and method of this invention are particularly suited to reaction systems that require a catalyst loading of at least about 1,000 kg of catalyst, based on total amount of catalyst located throughout the reaction system. In particular, the start up methods of this invention are particularly suited to reaction systems that require a catalyst loading of at least about 10,000 kg of catalyst, more particularly a catalyst loading of at least about 100,000 kg of catalyst, and most particularly a catalyst loading of at least about 250,000 kg of catalyst, based on total amount of catalyst located throughout the reaction system.

IV. Types of Solid Particles

The solid particles within the fluidized bed can be of any type that is useful for a desired reaction. In an embodiment, the solid particles are metal or metal oxide particles. In another embodiment, the solid particles comprise an active catalytic component, e.g., a metal, metal oxide, zeolite or silicoaluminophosphate, or combination thereof, that is incorporated with other formulation matrix materials into a solid, particulate catalyst in which the catalytically active component is present in an amount effective to catalyze the desired conversion reaction. The solid, particulate catalyst may include a catalytically effective amount of the active component and one or more formulation matrix materials, e.g., a filler material or a binder material, or both, to provide a desired property or properties, such as solid, particulate catalyst activity, particle size or particle size range, heat capacity, mechanical strength, attrition resistance, mesoporosity and the like, to the solid, particulate catalyst. The formulation matrix materials are desirably catalytically inert (do not promote conversion of the feedstock or the desired products), but are often to some extent porous in nature and have some nonselective catalytic activity to promote the formation of undesired products, or in other instances have desirable properties other than catalytic conversion of a hydrocarbon feedstock to desired products and also be considered a facilitating material. Such formulation matrix materials include, for example, synthetic and naturally occurring substances, metal oxides, clays, silicas, aluminas, alumina-halogen compounds, silica-aluminas, silica-magnesias, silica-zirconias, silica-thorias, silica-beryllias, silica-titanias, silica-alumina-thorias, silica-aluminazirconias, and mixtures of these materials. In one embodiment, a particular binder material utilized is the alumina-halogen compound aluminum chlorhydril, also known as aluminum hydroxychloride.

In an embodiment, the solid particles in the fluidized bed can be molecular sieve catalyst particles, where the solid particles are composed of a molecular sieve in combination with one or more matrix or binder materials as described above. Any variety of molecular sieves can be used to make the catalyst of this invention. Such molecular sieves include zeolites or non-zeolites.

Conventional crystalline aluminosilicate zeolites having catalytic activity are desirable molecular sieves that can be used in making the catalyst of this invention. Examples of such zeolite materials are described in U.S. Pat. Nos. 3,660,274 and 3,944,482, both of which are incorporated herein by reference. Non-limiting examples of zeolites which can be employed in the practice of this invention, include both natural and synthetic zeolites. These zeolites include zeolites of the structural types included in the *Atlas of Zeolite Framework Types*, edited by Ch. Baerlocher, W. M. Meier, D. H. Olson, Fifth Revised edition, Elsevier, Amsterdam, 2001, the descriptions of which are incorporated herein by reference.

Zeolites typically have silica-to-alumina ($SiO_2/Al_2O_3$) mole ratios of at least about 2, and have uniform pore diameters from about 3 to 15 Angstroms. They also generally contain alkali metal cations, such as sodium and/or potassium and/or alkaline earth metal cations, such as magnesium and/or calcium. In order to increase the catalytic activity of the zeolite, it may be desirable to decrease the alkali metal content of the crystalline zeolite to less than about 5 wt. %, preferably less than about 1 wt. %, and more preferably less than about 0.5 wt. %. The alkali metal content reduction, as is known in the art, may be conducted by exchange with one or more cations selected from the Groups IIB through VIII of the Periodic Table of Elements (the Periodic Table of Elements referred to herein is given in Handbook of Chemistry and Physics, published by the Chemical Rubber Publishing Company, Cleveland, Ohio, 45th Edition, 1964 or 73rd Edition, 1992), as well as with hydronium ions or basic adducts of hydronium ions, e.g., $NH_4^+$, capable of conversion to a hydrogen cation upon calcination. Desired cations include rare earth cations, calcium, magnesium, hydrogen and mixtures thereof. Ion-exchange methods are well known in the art and are described, for example, in U.S. Pat. Nos. 3,140,249; 3,142,251 and 1,423,353, the teachings of which are hereby incorporated by reference.

Examples of zeolites suitable for use in this invention include large pore zeolites, medium pore zeolites, and small pore zeolites. A large pore zeolite generally has a pore size of >7 angstroms and includes zeolite types such as MAZ, MEI, FAU, EMT. Examples of large pore zeolites include zeolite L, zeolite Y, zeolite X, offretite, omega, Beta, mordenite, ZSM-3, ZSM-4, ZSM-18, and ZSM-20. A medium pore size catalyst generally has a pore size <7 angstroms, preferably from about 5 angstroms to about 6.8 angstroms; and generally the pore apertures consist of about 10 to 12, preferably about 10, membered ring structures and include MFI, MEL, MTW, EUO, MTT, HEU, FER, and TON. Examples of medium pore zeolite include ZSM-34, ZSM-38, and ZSM-48. A small pore size zeolite has a pore size from about 3 angstroms to about 5.0 angstroms. Generally, the pore apertures of the structure consist of from about 8 to 10, preferably about 8, membered ring structures and include CHA, ERI, KFI, LEV, and LTA. Examples of small pore zeolite include ZK-4, ZK-5, zeolite A, zeolite T, gmelinite, chinoptilolite, chabasite and erionite. The zeolites can also comprise gallosilicates and titanosilicates.

In another embodiment, the molecular sieves are preferably metalloaluminophosphate molecular sieves that have a molecular framework that include [$AlO_4$] and [$PO_4$] tetrahedral units, such as metal containing aluminophosphates (AlPO). In one embodiment, the metalloaluminophosphate molecular sieves include [$AlO_4$], [$PO_4$] and [$SiO_4$] tetrahedral units, such as silicoaluminophosphates (SAPO).

Various silicon, aluminum, and phosphorus based molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624

(ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference.

In one embodiment, the molecular sieves are SAPO molecular sieves, and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the metalloaluminophosphate molecular sieve is represented, on an anhydrous basis, by the formula:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from the group consisting of Group IA, IIA, IB, IIIB, IVB, VB, VIB, VIIB, VIIIB and Lanthanide's of the Periodic Table of Elements. Preferably M is one or more metals selected from the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

In one embodiment of the invention, the metalloaluminophosphate molecular sieves are silicoaluminophosphate molecular sieves, containing silicon and aluminum. In general, lower Si/Al ratios lead to lower deactivation rates and higher ACIs for a given set of conditions. However, higher Si/Al ratios can be used under the appropriate conditions of temperature, water partial pressure and time of contact with water. Desirably, the solid particles are silicoaluminophosphate molecular sieves that contain Si and Al, at a Si/Al ratio of not greater than about 0.5, preferably not greater than about 0.3, more preferably not greater than about 0.2, still more preferably not greater than about 0.15, and most preferably not greater than about 0.1. In another embodiment, the Si/Al ratio is sufficiently high to allow for increased catalytic activity of the molecular sieve. Preferably, the solid particles are silicoaluminophosphate molecular sieves that contain Si and Al at a ratio of at least about 0.005, more preferably at least about 0.01, and most preferably at least about 0.02.

Non-limiting examples of SAPO and AlPO molecular sieves include one or a combination of SAPO-5, SAPO-8, SAPO-1, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference. For example, SAPO-18, AlPO-18 and RUW-18 have an AEI framework-type, and SAPO-34 has a CHA framework-type. Thus, the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

The solid particles can be of any size and shape suitable for fluidization, i.e., capable of being dynamically suspended by or carried along with a flow of gases within a reactor in order to form fluidized bed. The solid particles thus have a characteristic size relative to their density that is effective for fluidization. For example, embodiments include solid particles having a Geldart A or a Geldhart B classification. See Geldhart, D. (1973) Types of gas fluidization, *Powder Technology*, 7, 185-195. In various other embodiments, the solid particles have a particle size of less than about 20001μ, or from about 0.1μ to about 1,000μ, or from about 20μ to about 500μ, or from about 30μ to about 200μ. In other embodiments, the solid particles have a particle density of from about 50 pounds/cubic foot to about 200 pounds/cubic foot, or from about 70 pounds/cubic foot to about 150 pounds per cubic foot, or about 85 pounds per cubic foot to about 110 pounds per cubic foot. The solid particles in the fluidized bed can be of any conventional shape or size, including, but not limited to, those catalyst types made by spray drying, pelletizing, extrusion, and any of various conventional sphere-making techniques.

V. Examples of Various Embodiments of the Invention

A. Example of Suitable Apparatus for Solid Particle Sampling

Figure 3A:
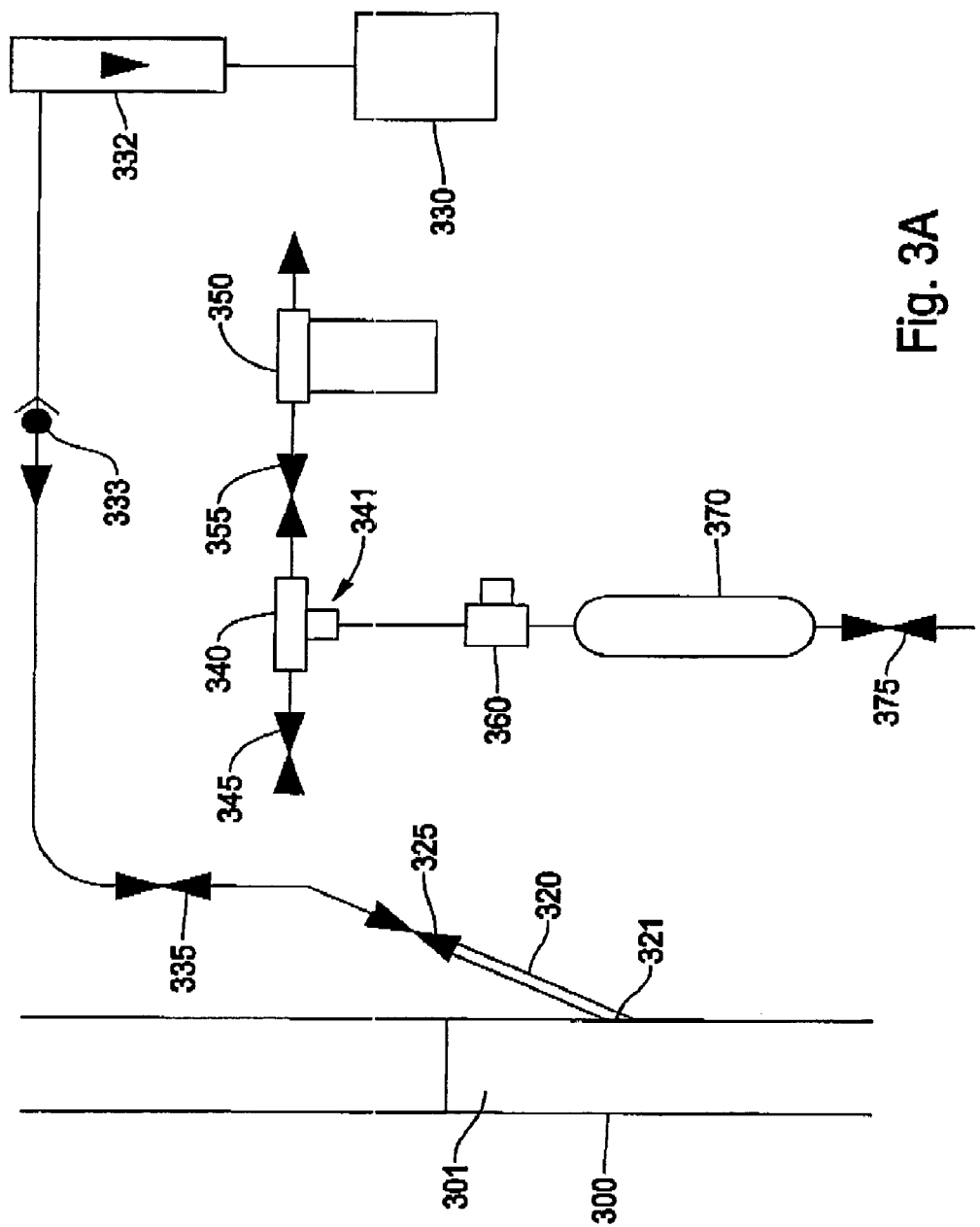
FIG. 3A schematically depicts a sampling system for collecting a sample of solid particles from a reactor having a fluidized bed wherein the sheltered volume, filter, and sample bomb are shown in the attached configuration.
Figure 3B:
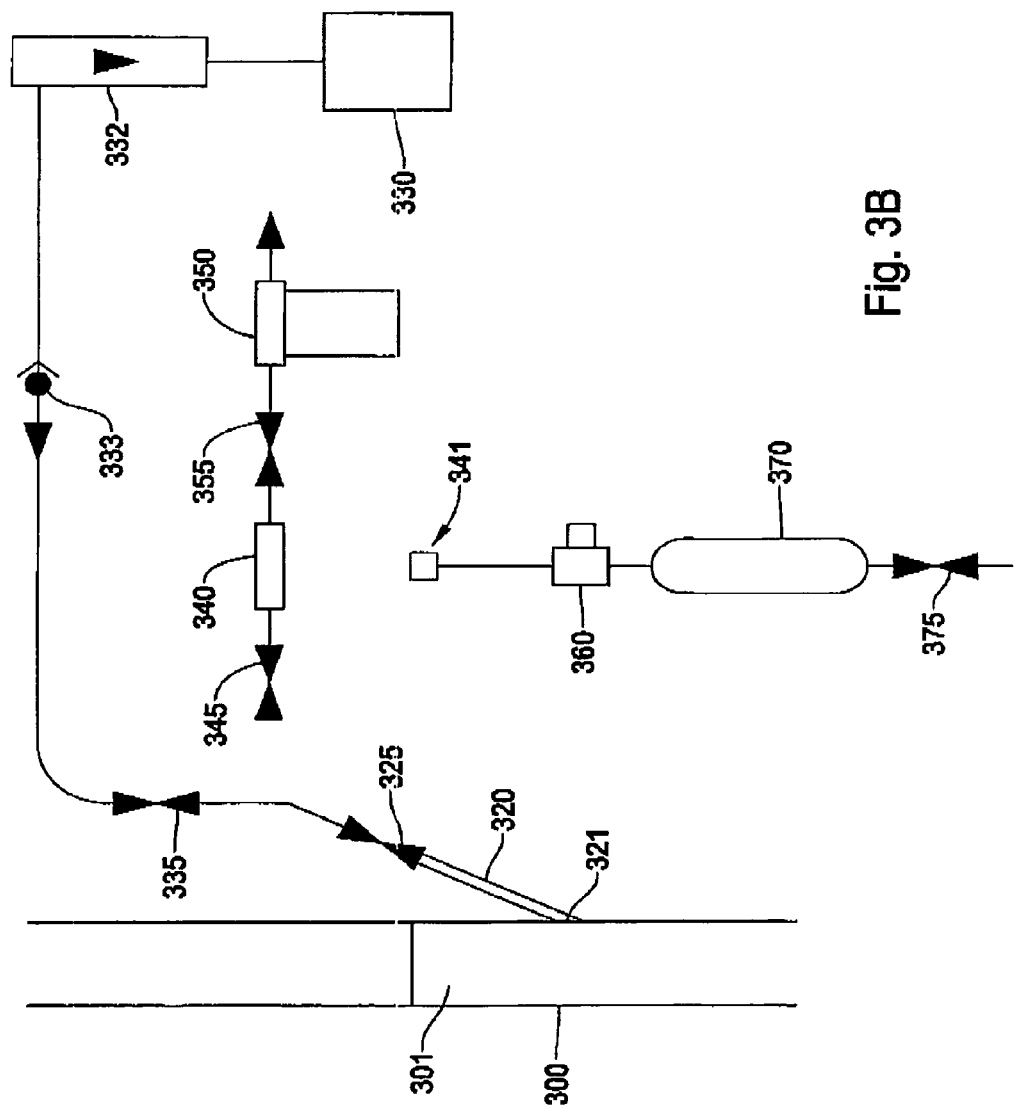
FIG. 3B schematic ally depicts a sampling system for collecting a sample of solid particles from a reactor having a fluidized bed wherein the sheltered volume, filter, and sample bomb are shown in the disconnected configuration.

FIG. 3 depicts an example of a collection system suitable for carrying out the present invention. Connections between elements shown in FIG. 3 can be made with any suitable conduit, such as 0.25 inch or 0.125 inch pipe. Reactor 300 contains a fluidized bed of solid particles 301. Particle intake valve 325 allows for isolation of the sample collector from bed 301. Particle intake valve 325 resides in particle intake conduit 320, which is openly connected to reactor 300 at inlet 321. Note that inlet 321 is located below the top level of bed 301.

In FIG. 3, sheltered volume 341 is located at a "T" intersection 340, where sampling valve 345 controls flow on one side of the T intersection 340, exhaust valve 355 controls flow on the far side of the T intersection 340, and the desired sample is collected in sheltered volume 341 at the bottom of the T. The bottom surface of sheltered volume 341 is a filter 360 that traps the solid particles while allowing gases to pass through. Similarly, exhaust filter 350 collects any solid particles that pass through exhaust valve 355. A sample bomb 370 is located below filter 360. Sample bomb pressure valve 375 controls the exit of gases from the sample bomb 370. In an embodiment, sheltered volume 341 can hold about 0.5 grams of solid particles.

A purge valve 335 controls the flow of purge gas from purge gas source 330 to the collection system. Purge gas source 330 must be able to deliver a sufficient pressure of purge gas so that particles residing in particle intake conduit 320 can be forced back into fluidized bed 301 during operation of the fluidized bed.

To collect a sample, sampling valve 345 and exhaust valve 355 are closed. Particle intake valve 325 and purge valve 335 are then opened. This forces purge gas into the fluidized bed. As a result, any particles residing in particle intake conduit 320 between inlet 321 and particle intake valve 325 are also forced back into the fluidized bed. This insures that the sample will contain particles representative of the current state of the fluidized bed. After removing any existing particles from the collection system, purge valve 335 is closed. Particle intake valve 325 and sampling valve 345 are then opened to allow solid particles into the sample collector, including sheltered volume 341. Inlet valve 325 is then closed and purge valve 335 and exhaust valve 355 are opened. This removes any excess solid not residing in sheltered volume 341. All of the valves are then closed to isolate the sample. Sample bomb pressure valve 375 is opened to relieve the pressure on the sample, and then sheltered volume 341 containing the sample is removed to allow for analysis of the sample.

B. Example of Full Sampling Cycle

The following provides an example how the processes of the present invention can be used in the apparatus shown in FIG. 3. Those skilled in the art will recognize that the method below can be employed in other systems, and that many variations on the method below are possible without departing from the scope and spirit of the invention.

1) Initial purge and verification—In an embodiment of the present invention, a sample collection cycle begins by removing any solid particles in the collection system that remain from previous samples. This procedure also allows the initial state of the collection system to be verified before the start of a sampling process. First, sampling valve 345 and exhaust valve 355 are closed. Particle intake valve 325 and purge valve 335 are then opened. This forces purge gas into the fluidized bed. As a result, any particles residing in particle intake conduit 320 between inlet 321 and particle intake valve 325 are also forced back into the fluidized bed. This insures that the sample will contain particles representative of the current state of the fluidized bed. Note that in preferred embodiments, inlet 321 is the lowest point relative to grade of particle intake conduit 320. An upward slope for particle intake conduit 320 reduces the likelihood of solid particles entering the collection system during the initial purge. A rotameter 332 can be used to verify the flow of purge gas from the purge gas source 330. In the event that purge gas source 330 cannot provide a sufficient pressure, check valve 333 limits the flow of particles toward purge gas source 330. Note that the portion of the collection system comprising sheltered volume 341, filter 360, and sample bomb 370 does not need to be attached during this procedure, as sampling valve 345 is closed.

In addition to the initial purge, any solid particles in sheltered volume 341 should also be removed. This can be accomplished by disconnecting sheltered volume 341 from the collection system and removing any solid particles.

2) Purge sampling bomb—Next, the sampling bomb is purged. Particle intake valve 325 is closed to isolate the collection system from the solid particle source. Sampling valve 345 and sample bomb pressure valve 375 are opened, while exhaust valve 355 remains closed. In this configuration, the only flow path available to the purge gas is through sheltered volume 341 to sample bomb 370 and sample bomb pressure valve 375. After purging, purge valve 335 is closed. Sample bomb pressure valve 375 is closed next, after the pressure in the sample bomb has equalized with the ambient pressure. The collection system is now ready to receive solid particles.

3) Collect sample of solid particles After verifying that primary exhaust valve 355 and sample bomb pressure valve 375 are closed, particle intake valve 325 is opened. Sample valve 345 is also opened at this time. Particle intake valve 325 only needs to stay open for long enough to fill the sheltered volume. This minimum time requirement wifl vary depending on the exact configuration. In the embodiment shown in FIG. 3, particle intake valve 325 is opened for 1 second. Particle intake valve 325 can be left open for a longer period of time without impacting the collection of solid particles in sheltered volume 341. However, allowing additional solid particles to accumulate in the collection system outside of sheltered volume 341 means that more particles will exit the collection system through exhaust valve 355 and become trapped in exhaust filter 350. The particles collected by exhaust filter 350 can be recycled, however.

4) Remove excess particles—After closing particle intake valve 325, purge valve 335 and exhaust valve 355 are opened. This allows purge gas to flow through the collection system from purge gas source 330 through purge gas valve 335 to exhaust valve 355. Any solid particles along this flow path are swept into exhaust filter 350. This removes the excess catalyst, leaving behind only the catalyst in sheltered volume 341. Sampling valve 345 and exhaust valve 355 are closed after this purge step. Sample bomb pressure valve 375 is then opened to relieve any pressure that has built up in the sample bomb. After relieving the pressure, the sheltered volume, filter, and sample bomb are disconnected from the collection system to harvest the sample. Note that sheltered volume 341 should be kept upright during removal to prevent loss of any solid particles.

Using the above method in conjunction with an apparatus such as the one depicted in FIG. 3 has a number of advantages. First, the method allows for sample collection with only a minimal amount of loss to the particle bed. For example, if the sample collector uses quarter-inch pipe, the entire sample size collected in the sheltered volume will only be 0.5 grams. This reduces the amount of recycling (or other addition of particles) required for the solid particles. The method also allows for frequent sampling. The total time for collecting a sample is under 5 minutes. This allows for frequent monitoring of a process, such as to check the coking level of a catalyst in an MTO process.

Having now fully described this invention, it will be appreciated by those skilled in the art that the invention can be performed within a wide range of parameters within what is claimed, without departing from the spirit and scope of the invention.

We claim:

1. A method of collecting a predetermined volume of a solid material in particulate form having a particle density of from about 50 to about 200 pounds/cubic foot, from a reactor system, comprising the steps of:
    a) receiving solid material from a reactor system;
    b) collecting the solid material in a sample collection system;
    c) passing a gas through an unsheltered volume within the sample collection system to remove a portion of the solid material from the sample collection system;
    d) leaving a predetermined volume of the solid material within a sheltered volume within the sample collection system as the gas is passed through the collection system; and
    e) extracting the predetermined volume of the solid material left within the sample collection system.

2. The method of claim 1, further comprising purging the collection system prior to receiving the solid material from the reactor system.

3. The method of claim 1, wherein the solid material is received from a reaction system selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing ammatics, systems for converting oxygenates to olefins, systems for converting oxygenates to aromatics, systems for oligomerizing olefins, and systems for converting unsaturated hydrocarbons to aldehydes.

4. The method of claim 1, wherein the solid material is received from a catalytic cracking reactor.

5. The method of claim 1, wherein the solid material is received from a fluidized bed reaction system, a fast fluidized bed reaction system, a circulating fluidized bed reaction system, or a riser reactor system.

6. The method of claim 1, wherein the receiving the solid material comprises receiving solid particles containing a catalytically active component and a matrix material.

7. The method of claim 6, wherein the received solid particles contain a catalytically active component selected from the group consisting of metal, metal oxide, zeolites, silicaaluminophosphates, and molecular sieves.

8. A method for sampling solid particles having a narticle density of from about 50 to about 200 pounds/cubic foot. comprising the steps of:
    a) receiving a sample of solid particles by entraining the sample of solid particles within a gas flow and drawing the entrained solid particles into a collection system, wherein the sample comprises a first portion collected in a sheltered volume within said collection system, and a second portion;
    b) separating the second portion of the sample from the first portion of the sample within said collection system; and
    c) extracting the first portion of the sample from said collecting system.

9. The method of claim 8, wherein the first portion of the sample is collected in a sheltered volume having a size corresponding to a predetermined sample volume.

10. The method of claim 8, wherein the sample of solid particles is received from a reaction system selected from the group consisting of catalytic cracking reaction systems, transailcylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates to olefins, systems for converting oxygenates to aromatics, systems for oligomerizing olefins, and systems for converting unsaturated hydrocarbons to aldehydes.

11. The method of claim 8, wherein the sample of solid particles is received from a catalytic cracking reactor.

12. The method of claim 8, wherein the sample of solid particles is received from a fluidized bed, a fast fluidized bed, a circulating fluidized bed, or a riser reactor.

13. The method of claim 8, wherein the received solid particles contain a catalytically active component and a matrix material.

14. The method of claim 13, wherein the received solid particles contain a catalytically active component selected from the group consisting of metals, metal oxides, zeolites, silicaaluminophosphates and molecular sieves.

15. An apparatus for obtaining a sample of solid particles, comprising:
    a) a particle intake conduit connected to a source of solid particle within a reactor, said solid particles having a particle density of from about 50 to about 200 pounds/ cubic foot;
    b) a sheltered volume connected to the particle intake conduit, wherein the connection between the particle intake conduit and the sheltered volume defines a first flow path;
    c) a purge source connected to the first flow path between the particle intake conduit and the sheltered volume; and d) an exhaust connected to the first flow path, wherein the connection between the exhaust and the first flow path defines a second flow path, at least a portion of the first flow path and the second flow path are in common, and the second flow path does not pass through the sheltered volume.

16. The apparatus of claim 15, wherein the sheltered volume comprises a filter having smaller mesh size than the average diameter of the solid particles.

17. The apparatus of claim 15, wherein the particle intake conduit is connected to the solid particle source via a sample intake valve.

18. The apparatus of claim 15, wherein the solid particle source is a fluidized bed, a fast fluidized bed, a circulating fluidized bed, or a riser reactor.

19. The apparatus of claim 15, wherein the solid particle source is a reaction system selected from the group consisting of catalytic cracking reaction systems, transailcylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for convening olefins to distillate, systems for converting olefins to lubes, systems for converting alcohols to olefins, disproportionation reaction systems, systems for converting aromatics to higher aromatics, systems for adsorbing aromatics, systems for converting oxygenates to olefins, systems for converting oxygenates to aromatics, systems for oligomerizing olefins, and systems for converting unsaturated hydrocarbons to aldehydes.

20. The apparatus of claim 15, wherein the solid particle source comprises solid particles containing a catalytically active component and a matrix material.

21. The apparatus of claim 20, wherein the solid particles contain a catalytically active component selected from the group consisting of metals, metal oxides, zeolites, silicaaluminophosphates, and molecular sieves.

22. The apparatus of claim 15, wherein the sheltered volume is connected to the particle intake conduit via a sampling valve.

23. The apparatus of claim 15, wherein the intersection of the exhaust, first flow path, and sheltered volume forms a T-intersection.

24. The apparatus of claim 15, wherein the common portion of the flow paths is immediately adjacent to the sheltered volume.

25. A method for obtaining a sample of solid particles, the method comprising the steps of:
a) providing a collection system comprising a particle intake conduit connected to a source of solid particles having a particle density of from about 50 to about 200 pounds/cubic foot, a source of purge gas, an exhaust, a sheltered volume, a first flow path connecting the particle intake conduit to the sheltered volume, and a second flow path connecting the source of purge gas and the exhaust, wherein at least a portion of the first flow path and second flow path are in common, and wherein the second flow path does not pass through the sheltered volume;
b) receiving a sample of solid particles into the sheltered volume via the first flow path;
c) flowing purge gas through the common portion of the flow paths; and
d) extracting the sample of solid particles from the sheltered volume.

26. The method of claim 25, wherein receiving the sample of solid particles comprises opening a particle intake valve for one second, wherein the particle intake valve connects the particle intake conduit to the source of solid particles.

27. The method of claim 25, wherein the sample is extracted from the sheltered volume by disconnecting the sheltered volume from the collection system.

28. The method of claim 25, further comprising purging the collection system prior to receiving the sample of solid particles.

29. The method of claim 25, wherein the sample of solid particles is received from a reaction system selected from the group consisting of catalytic cracking reaction systems, transalkylation reaction systems, isomerization reaction systems, catalytic dewaxing systems, alkylation reaction systems, hydrocracking reaction systems, systems for converting paraffins to olefins, systems for converting paraffins to aromatics, systems for converting olefins to gasoline, systems for converting olefins to distillate, systems for converting olefins to lubes, systems for converting alcohols to olefins, disproportionation reaction systems, systems for converting aromatics to higher aromatics, systems for adsorbing aromatics, systems for converting oxygenates to olefins, systems for converting oxygenates to aromatics, systems for oligomerizing olefins, and systems for converting unsaturated hydrocarbons to aldehydes.

30. The method of claim 25, wherein the sample of solid particles is received from a catalytic cracking reactor.

31. The method of claim 25, wherein the sample of solid particles is received from a fluidized bed, a fast fluidized bed, a circulating fluidized bed, or a riser reactor.

32. The method of claim 25, wherein the received solid particles contain a catalytically active component and a matrix material.

33. The method of claim 32, wherein the received solid particles contain a catalytically active component selected from the group consisting of metals, metal oxides, zeolites, silicaaluminophosphates, and molecular sieves.

* * * * *